(12) United States Patent
Bobbert

(10) Patent No.: US 8,865,226 B2
(45) Date of Patent: Oct. 21, 2014

(54) LOW FOAMING ENHANCED BIOCIDAL HYDROGEN PEROXIDE COMPOSITION

(75) Inventor: Ilja Bobbert, Hilversum (NL)

(73) Assignee: Aseptix Research BV, Loenen Aan de Vecht (NL)

( * ) Notice: Subject to any disclaimer, the term of this patent is extended or adjusted under 35 U.S.C. 154(b) by 1583 days.

(21) Appl. No.: 12/226,657

(22) PCT Filed: Apr. 27, 2007

(86) PCT No.: PCT/EP2007/054164
§ 371 (c)(1),
(2), (4) Date: Nov. 20, 2009

(87) PCT Pub. No.: WO2007/125101
PCT Pub. Date: Nov. 8, 2007

(65) Prior Publication Data
US 2010/0068295 A1    Mar. 18, 2010

(30) Foreign Application Priority Data

Apr. 27, 2006    (EP) .................................... 06113228

(51) Int. Cl.
*A01N 59/00*    (2006.01)
*A01P 1/00*    (2006.01)

(52) U.S. Cl.
CPC ...................................... *A01N 59/00* (2013.01)
USPC ......................................................... 424/616

(58) Field of Classification Search
CPC ... A01N 59/00; A01N 2300/00; A01N 25/30; A01N 37/36
USPC ............... 424/616; 435/320.1, 6.16; 536/23.1
See application file for complete search history.

(56) References Cited

U.S. PATENT DOCUMENTS

| 6,444,230 B1 | 9/2002 | Godin et al. |
| 2005/0019421 A1 * | 1/2005 | Hobbs et al. .................. 424/616 |

FOREIGN PATENT DOCUMENTS

| EP | 0 268 873 A2 | 6/1988 |
| EP | 0 423 922 A1 | 4/1991 |
| JP | A 64-061427 | 3/1989 |
| JP | 09137192 A * | 5/1997 |
| JP | A-09-137192 | 5/1997 |
| JP | A 2001-072996 | 3/2001 |
| JP | 2009137192 A * | 6/2009 |
| JP | A-2009-137192 | 6/2009 |
| WO | WO 97/28691 A1 | 8/1997 |
| WO | WO 98/00485 A1 | 1/1998 |
| WO | WO 00/35289 A1 | 6/2000 |
| WO | WO 02/50233 A1 | 6/2002 |
| WO | WO 03/067989 A1 | 8/2003 |

OTHER PUBLICATIONS

Nobuyuki et al., Liquid bleaching agents, ChemicalAbstracts Service, Aug. 1, 1997, vol. 127, No. 6.*
Nobuyuki et al., "Liquid bleaching agents," *Chemical Abstracts Service*, Aug. 11, 1997, vol. 127, No. 6, Columbus, Ohio, USA.
Apr. 25, 2007 European Search Report issued in corresponding European Patent Application No. 06 118 497.4.
Office Action dated Jun. 6, 2012 issued in Japanese Patent Application No. 2009-507090.

* cited by examiner

*Primary Examiner* — Janet Epps-Smith
*Assistant Examiner* — Courtney Brown
(74) *Attorney, Agent, or Firm* — Oliff PLC

(57) ABSTRACT

The present invention discloses a biocidal composition comprising hydrogen peroxide in a concentration of 0.05-50% (w/w) and a compound with a structure according to Formula 1: $R-O-(CH(Y)-CH_2-O)_n-CH_2-COOH$, wherein R is an alkyl or alkenylene radical containing 6-12 carbon atoms, Y is H or $CH_3$, and n is 3-10, in a concentration of 0.01-60% (w/w). An especially preferred compound according to Formula 1 is R is 6 or 8 and n is 3-8.

25 Claims, No Drawings

LOW FOAMING ENHANCED BIOCIDAL HYDROGEN PEROXIDE COMPOSITION

The present invention relates to the field of disinfection and cleaning, more specifically to a low foaming enhanced biocidal activity compositions based on hydrogen peroxide.

Numerous classes of chemical compounds exhibit varying degrees of biocidal or antimicrobial activity. Biocidal compositions are needed, among other things, to clean and disinfect food surfaces such as fruits and vegetables and to clean and disinfect hard-surfaces in the health care industry, food and beverage industries and household area.

In the past few years, efforts have been concentrated on developing chemicals that will be highly effective against microorganisms when in a diluted form, will be low in toxicity to humans and other animals, and will not be harmful to the environment.

Of the known disinfectants and biocidals, hydrogen peroxide appears to have exceptional potential, because the decomposition products, water and oxygen, are not toxic and not harmful to the environment. Also, it tends to have a broad spectrum biocidal, activity. Broad spectrum activity is important for instance in situations where harmful organisms are present but their identity is not known. Hydrogen peroxide-based disinfectants are useful in many different applications, including in hospitals, clinics, laboratories, dental offices, home care and chronic care facilities. They may also be used in food and beverage processing and preparation, animal husbandry, the hospitality industry and for general sanitation.

In order to provide fast, effective action, biocidal hydrogen peroxide solutions had to employ relatively high concentrations of hydrogen peroxide. However, at higher concentrations, the solutions may be subject to hazardous goods regulations and may require special precautions for handling and use. For example, at concentrations of above about 8 w/w % aqueous solution, hydrogen peroxide is considered corrosive and is also a strong oxidizing agent. Solutions containing less than about 8 w/w % hydrogen peroxide are preferred for their improved safety profile.

Compositions based on hydrogen peroxide as the only biocidal compound and containing up to 7% hydrogen peroxide by weight of the total composition are not fully efficacious to disinfect soiled surfaces, e.g., surfaces which needs both to be washed and disinfected. Indeed, the presence of organic and/or inorganic soils decreases the bactericidal activity of many antimicrobials like peroxygen-based agents, resulting thereby in a lower bactericidal activity and disinfection power of compositions comprising them.

At low concentrations (e.g. 3% w/w), hydrogen peroxide is non-irritating to skin, but exhibits low germicidal activity. For example, a solution containing 3% w/w hydrogen peroxide takes 20 minutes to achieve a greater than 6 log reduction in *Staphylococcus aureus*, which is too long for many applications. Increasing the concentration of hydrogen peroxide will increase the rate of disinfection. For example, a 25% w/w aqueous solution of hydrogen peroxide requires only 20 seconds to achieve a greater than 6 log reduction in *Staphylococcus aureus*. However, the solution is corrosive at this concentration and requires special handling procedures.

In order to make an antimicrobial composition that can be effectively used in non-industrial situations or even in household situations, the composition must have a set of properties to be technically and commercially attractive. These properties are as follows: appropriate biocidal activity, as low as possible concentration of active ingredients, no pungent odors, non-corrosive to materials and skin, easy-to-apply and applicable without rinsing. The latter feature requires the composition to be low foaming.

Several solutions are proposed in the art to obtain hydrogen peroxide compositions with enhanced biocidal activity. However, these solutions do not adequately deal with the problem to achieve very good disinfectant results and at the same time have a positive effect on the wetting properties without having high foam characteristics. Highly foaming compositions might cause problems in various situations, for instance where the compositions are used via equipment or devices, such as pumps, nozzles, aerosol devices or spray-heads. Due to the turbulent motion of the cleaning and disinfecting solution resulting from pumping, spraying and other processes, agents and solutions that tend to produce foam are completely unsuitable, although being recommended for use in disinfecting compositions.

For this reason, in practice the use of agents that contain highly foaming surfactants, such as sulfonic acids, ethersulfates, sulfosuccinates or sulfonates, are basically to be avoided in the context of so-called cleaning in place (CIP) processes.

In addition, the wetting characteristics of the biocidal composition are of especial importance. Bacterial problems often occur in disinfection processes when, although sufficient active disinfectant is used, it does not reach the surface to be disinfected or does not adhere to this surface for a sufficiently long time period, due to low wetting power.

Complete wetting at the required application concentration, with the maintenance of a minimum contact time, is absolutely necessary for reliable destruction of all harmful micro-organisms.

It is known that surfactants are able to increase wetting capacity of solutions. However, it is also known that many surfactants, due to their strong wetting effect, exhibit very intense foaming behaviour under the conditions of application. As indicated before, in many disinfectant applications, foaming disinfectant solutions cannot be used or have disadvantages in use. Especially where the disinfectant solution is used inside equipment, pumps, spray nozzles, etc. or where no or very low rinsing is required.

For instance, the compositions disclosed in WO 03/067989, comprising certain anionic sulfonic acid-based surfactants and hydrogen peroxide, although highly effective as disinfecting compositions, are not suitable for applications where low-foaming is required.

It is therefore an object of the present invention to provide compositions which deliver excellent biocidal activity using as low as possible hydrogen peroxide concentrations and/or as less as possible further (biocidal) additives. Also, an objective has been to provide a composition that can be applied without handling or usage precautions and safety measures, and that does not require rinsing or only scarce rinsing after application. It has also been an object of this invention to prepare a synergistic broad spectrum biocidal solution without the use of peracetic acid, which causes a pungent odor and is not advisable to use in domestic cleaning, skin disinfection, food processing, mouth care and personal care applications.

It is surprisingly shown by the present invention that compositions comprising a combination of hydrogen peroxide and certain alkylether carboxylic acids show an enhanced biocidal activity, a low foaming behaviour and still possess a good wetting capacity.

The compositions of the invention do not need inclusion of disinfectants like peracetic acid and/or acetic acid, making the odor of the compositions much more acceptable for nonprofessional applications, while the broad spectrum antimicrobial efficacy is still sufficient to reach the required industry norms.

WO 97/28691 discloses a quick acting room temperature disinfectant solution primarily useful for disinfecting medical instruments. The composition comprises hydrogen peroxide and from about 1% to 30% by weight of a water soluble organic acid or salt form thereof with the acid preferably being selected from the group consisting of malonic and succinic acids. A surfactant may optionally be included, among which alkyl sulfates, amine oxides and alkyl polyethoxy carboxylate salts, with an alkyl group of 8 to 22 carbon atoms and from 0-10 ethoxy groups. An exemplified surfactant is a sodium olefin sulfonate.

EP 0 423 922 discloses an antimicrobial surface sanitizing composition comprising an α-hydroxy substituted mono- or di-carboxylic acid, preferably lactic acid, and hydrogen peroxide, wherein after contact with the intended surface said antimicrobial composition leaves a noncontaminating residue upon that surface. A surfactant, for instance a polyalkyloxycarboxylate or a sulfonate, may further be included in the composition.

U.S. Pat. No. 6,444,230 discloses improved antimicrobial activity of the combination of a peroxygen compound with an amine oxide. Optionally, an ethoxylated carboxylic ether may be included in the composition. However, U.S. Pat. No. 6,444,230 thereby emphasizes that the excellent fungicidal results are due to the synergism induced by the presence of peracetic acid and an amine oxide in the same composition.

WO 02/50233 discloses a composition aimed at CIP disinfection comprising a surfactant combined with a percarboxylic acid. The surfactant preferably is a alkylbenzene sulfonic acid or sulfonate and/or an ethercarboxylic acid. Exemplified is a composition comprising a high amount of acetic acid, hydrogen peroxide, a C10-C13 alkylbenzene sulfonic acid and an unspecified ethercarboxylic acid.

JP 9-137192 discloses a liquid bleaching agent comprising hydrogen peroxide, a specific bleaching activator and a specific polyoxyalkylene compound. Among the polyoxyalkylene compounds, ethercarboxylic acids may be chosen. These ethercarboxylic acids may have an alkyl or alkylene group of 1-20 C-atoms and may have 1-50 alkylene oxide units. Two exemplified ethercarboxylic acids have 14 and 20 ethoxy groups, respectively, and a C12 alkyl or a C18 alkenylene group, respectively. The examples thus show a clear preference for long tailed molecules. This is because long tailed molecules naturally can fulfil an important role in a bleaching composition to solubilise stains and keep the particles suspended. It is a specific preference of the current invention to have relatively short carbon chains (C6-C12) and a low alkoxylation degree (n is 3-10), to balance foaming behaviour, biocidal activity and synergistic activity with hydrogen peroxide in antimicrobial applications.

Thus, in a first aspect, the present invention provides a composition comprising hydrogen peroxide in a concentration of 0.05-50% (w/w) and a compound with a structure according to Formula 1:

R—O—(CH(Y)—CH$_2$—O)$_n$—CH$_2$—COOH, wherein R is an alkyl or alkenylene radical containing 6-12 carbon atoms, Y is H or CH$_3$ and n is 3-10, in a concentration of 0.01-60% (w/w), with the provision that the composition does not contain acetic acid at a concentration of 0.001% or higher and/or peracetic acid at a concentration of 0.0005% or higher.

Preferably, R is a straight chain alkyl radical. Also preferably, R is an alkyl radical of 6-10 carbon atoms, more preferably of 6-8 carbon atoms.

An individual compound with a structure according to Formula 1 may further contain only propoxy or only ethoxy groups or may contain a mixture of ethoxy and propoxy groups. Preferably, n is 3-8 and/or Y is H.

Such a composition surprisingly has an excellent biocidal activity, even upon dilution to a composition comprising 0.1-8% of hydrogen peroxide and 0.01-10% of a compound with a structure according to Formula 1. The combination of hydrogen peroxide and the compound according formula 1 provides a more potent biocide than that can be obtained by using these two compounds separately. The composition has good wetting properties and does not produce excessive foam.

Unless indicated otherwise, percentages used throughout this invention are weight percentages based on the total weight of the composition.

It will be apparent to the skilled person that mixtures of compounds according to Formula 1 are also encompassed in the present invention. An example of such a mixture comprises a compound according to Formula 1 with Y is H, and with R is C8 and n is 8 and with R is C6 and n is 3.

Preferred structures according to Formula 1 are structures wherein Y is H, R is a straight chain C6 and n is 3; R is a straight chain C8 and n is 8; R is a straight chain C8 and n is 5, and combinations thereof. These preferred structures according Formula 1 are provided for instance by the surfactants marketed under the trade names AKYPO LF1, LF2, LF4 and LF6 (from KAO Chemicals).

The composition of the invention preferably may be sold as a concentrate comprising hydrogen peroxide in a concentration that may range from about 10-50% and the compound with a structure according to Formula 1 in a concentration that may range from about 5-60%. Said concentrate may suitably be diluted to the effective concentration to be used in the final application.

Upon dilution, the effective hydrogen peroxide concentration of the composition of the invention may be 0.05-8% (w/w), preferably 0.1-5%, more preferably 0.2-3%, most preferably 0.3-2%. Depending on the intended use of the composition of the invention, the hydrogen peroxide concentration may be in the higher range, e.g. from 1-8%, or in the lower range, e.g. from 0.05-1%. The concentration of the compound with a structure according to Formula 1 may be 0.01-10% (w/w), preferably 0.02-5%, more preferably 0.05-2%.

The concentration of hydrogen peroxide and the compound with a structure according to Formula 1 in the composition of the invention preferably is chosen in such a way that the weight ratio between hydrogen peroxide and the compound with a structure according to Formula 1 varies between 10 and 0.1, more preferably between 5 and 0.2, most preferably between 2 and 0.5.

Compounds with a structure according to Formula 1 have several advantages to be particularly useful in the applications as described herein. In acidic, aqueous solutions the compounds with a structure of Formula 1 behave like nonionic surfactants. In neutralised form they behave like anionic surfactants (the crypto-anionic character of alkylethercarboxylic acids). It was found that in combination with hydrogen peroxide, the nonionic behaviour in the slightly acidic ranges provides for a simple, but highly synergistic blend, with high antimicrobial activity and enhanced wetting capacity.

A major advantage of the compositions comprising a structure according Formula 1 is that the low foaming behaviour is seen at different temperatures, whereas with nonionic surfactants such foam levels only occur at around the cloud point.

This makes them particularly useful in situations whereby the composition is used as rinsing liquid in food-, beverage-, ice cream-, and dairy processing industries.

Due to the effectiveness of the combination of hydrogen peroxide and the compound with a structure according to Formula 1, the composition of the invention may be used as a formulation which is as simple as possible. For many applications it may not be necessary to supplement the composition of the invention with additional compounds influencing (enhancing) its biocidal activity. Thus, in such embodiments, the composition of the invention consists essentially of hydrogen peroxide and the compound with a structure according to Formula 1 as compounds with biocidal activity.

The biocidal activity of a composition of the invention is determined by a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements).

Advantageously, the composition of the invention not only displays good bactericidal activity, but also good fungicidal, mycobacteridal and virucidal activity.

The biocidal peroxide composition of the invention preferably is an aqueous solution.

In a preferred embodiment, the biocidal peroxide composition of the invention is a ready-to-use aqueous solution comprising 0.1-5% hydrogen peroxide and 0.05-5% of a compound with a structure according to Formula 1, such as AKYPO LF4 of KAO Chemicals. The pH of the solution preferably is 1-7, more preferably 1.5-6, most preferably 1.5-5.

Such composition also is very ecologically friendly.

In one embodiment of the invention, the composition of the invention is supplemented by compounds enhancing its practical utility, such as non-ionic, cationic, and/or anionic surfactants, solvents, stabilizers, preservatives, coloring agents, fragrances, etc.

For instance, a pH adjusting acid (organic or inorganic) or base or an appropriate buffer may suitably be added to provide the composition of the invention with a pH of choice. A suitable acid for adjusting the pH for instance is citric acid or potassium hydroxide. Preferably, the composition of the invention has a pH in the acidic region, more preferably a pH of 1-7, even more preferably a pH of 1.5-6, and most preferably a pH of 1.5-5.

The composition of the invention further may comprise a hydrogen peroxide stabilizer, preferably in the form of a cation sequestering agent, more preferably in a concentration of 0.01 to 20% (w/w). The cation sequestering agent may be chosen from ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), and salts thereof or from benzoic acid, aminobenzoic acid, citric acid, phosphoric acid, iminodisuccinic acid and polyaspartic acid. More preferably, the cation sequestering agent is a (colloidal) stannate, and even more preferably is chosen from acetanilide, trisodium ethylenediamine disuccinate, for instance OctaQuest E30 or A65 (Octel), phosphonic acid derivatives having 1 to 5 phosphonic acid groups, for instance a Dequest phosphonate (Solutia), 1-hydroxyethylidene-1,1-diphosphonic acid, amino tri(methylene phosphonic acid), diethylenetriamine-penta(methylene phosphonic acid), 2-hydroxy ethylimino bis(methylene phosphonic acid), and ethylene diamine tetra(methylene phosphonic acid).

The composition of the invention further may comprise a corrosion inhibitor, preferably, in a concentration of 0.01% to 20% w/w. Preferably, the corrosion inhibitor is chosen from 1,2,3 benzotriazole, sodium molybdate, sodium nitrite, sodium bisulfate, sodiummetabisulfate, chromates, borates, phosphates, polyphosphates, sodium benzoate, sodium gluconate and sodium silicate.

The composition may also comprise a hydrogen peroxide compatible surfactant. This surfactant may be an anionic, a cationic, a nonionic and/or an amphoteric surfactant, preferably a nonionic and/or cationic and/or an anionic surfactant. The surfactant concentration may be from 0.005 to 40% w/w.

Exemplary hydrogen peroxide compatible nonionic surfactants are ethoxylated alcohols, alkyl polyalkylene glycol ethers and alkylpolyglucosides having a hydrophile lyophile balance from 5 to 15 and/or sufficiently water-soluble block copolymers of ethylene oxide or propylene oxide, a C6-C14 alkyl, 3-8 moles of ethylene oxide (EO) alcohol ethoxylate, or a combination thereof.

Exemplary hydrogen peroxide compatible anionic surfactants, of which the low foaming types are most preferred, are alkyl sulfates, e.g. C8-C16 alkyl sulfates, C8-C16 alkyl phosphates, alkyl ether sulfates, alkyl benzene sulfonic acids, e.g. alkali metal, alkaline earth metal, ammonium or alkylamine salts of C8-C16 alkyl benzene sulfonic acids, alkyl sulfonic acids, e.g. C8-C18 alkyl sulfonic acids, alkyl diphenyl oxide sulfonic acids, C6-C12 alkyl diphenyl sulfonates, naphthalene sulfonic acids, alkyl or alkenyl esters or diesters of sulfosuccinic acids, and salts thereof.

Preferred surfactants may also be chosen from the group of alkyl betaines, alkyl amidopropyl betaine amides, alkyl amidopropyl betaines, amine oxides, and derivates thereof, in a concentration of about 0.01-40% w/w.

As well, the composition may comprise at least one C1 to C8 alcohol, preferably in a concentration of about 0.01 to about 10% w/w. The alcohol may be chosen from benzyl alcohol, ethanol, n-butanol, propanol, isopropanol and glycols, such as ethylene glycol, propylene glycol and butylene glycol.

Other additives may be added to the biocidal peroxide composition of the invention in order to provide the composition with properties suitable for its use. Examples of such additives are emulsifiers, hydrotropes, glycerol, thickening agents, fragrances, coloring chemicals, preservatives and anti-foam.

In another aspect, the present invention relates to the use of the biocidal hydrogen peroxide composition of the invention for any purpose where disinfecting and/or sanitizing and/or preservative activity is required, optionally combined with cleaning and/or bleaching activity, including, but not limited to, use as a biocidal and sterilization liquid, and as disinfection and sanitization agent.

In particular, the biocidal peroxide composition of the invention may be used for those applications where it is important to obtain disinfecting and/or sanitizing and/or preservative activity with the mildest agents possible, for instance domestic use, medical use, personal care, mouth care, food, clean rooms, etc. Also for applications where no or scarce rinsing after application is preferred, or where the solution may come into contact with food.

Since the biocidal peroxide composition of the invention is non-irritating, has no odors or volatile gasses, and is skin friendly, it is also optimal for situations where users do not wear any protective clothing, in cases where worker-safety has high priority or for personal application like wound disinfection or prevention of gingivitis.

The composition of the present invention may be used singly or in combination with the compounds as described herein as low-foaming composition for applications in household-, professional- and institutional areas. They are very user-friendly because of the following properties: hardwater stable, electrolyte stable, enhanced corrosion prevention, and mildness to the skin.

Furthermore the composition of the present invention is especially suitable for situations whereby intense foam behavior is undesired, such as with cleaning in place processes and with disinfecting of devices and surfaces in medical field and the food, dairy, poultry, meat, fish and soft drink industries.

Thus, the present invention relates to the use of the composition of the invention for disinfecting and/or sanitizing and/or preserving a substrate. This can be done by contacting the substrate with an effective amount of the biocidal composition of the invention. The contacting may be done by spraying, dipping, fogging and/or rinsing. In addition to disinfection, the composition is especially effective in the removal of stains and dirt. The substrate may be any surface, space, material, animate object and/or inanimate object. For instance, the substrate may be a medical instrument or device, hospital or industrial equipment, surface of walls, ceilings and/or floors, a food product, an agricultural product, human or animal skin, etc. Preferably, the substrate is a substrate wherein the presence of (pathogenic) micro-organisms is suspected.

The composition of the invention may be effectively used for food preservation, as rinsing liquid in breweries and dairy production, for veterinary and cattle applications, such as prevention and treatment of mastitis, and for water treatment and water disinfection. A preferred use of the composition of the invention relates to the application of the composition for rinsing of fruit, vegetables, fish, poultry and meat. Due to the low foam and low rinsing requirement, the composition of the present invention may be advantageously used for applications in food processing and antimicrobial rinsing liquid.

When used in neutral household or non-industrial cleaners, the good dermatological properties of the compounds with a structure according Formula 1 come fully into play. The compositions of the current invention comprising compounds according Formula 1 and hydrogen peroxide are further readily biodegradable in accordance with the OECD guidelines.

The present invention also relates to the use of the biocidal peroxide composition in specific devices such as spray devices, e.g. spray bottles, aerosol cans, aerosol generation devices for room disinfection, and by application in the form of dipping.

A further use of the biocidal hydrogen peroxide composition of the present invention relates to the use as skin disinfecting agent, preferably for hand disinfection.

The composition of the invention is able to provide adequate levels of disinfection while not being irritating to the skin. The composition is non-irritating due to the low levels of hydrogen peroxide, mild properties of the structure according Formula 1, and low concentrations of other mild additives that may be employed as described above.

Another use of the composition of the invention relates to the use in dentistry and as mouth rinse. Infection and inflammation control in the mouth and oral cavities is still an important area and until today dominated by chlorine-, alcohol- and phenol-based products. Many of these products have significant drawbacks and have a negative influence on living tissue. The compositions of the present invention can effectively replace such products.

In order to have an effective composition for dentistry and mouth rinse, various compounds may be added to the composition of the invention to enhance its anti-microbial efficacy, such as anti-microbial essential oils and zinc salts, i.e. zinc chloride, zinc oxide, zinc lactate, or compounds that enhance the practical utility such as glycols, alcohols, edible surfactants, flavors, fragrances, etc.

EXAMPLES

Bactericidal activity of the exemplified compositions was tested using a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements). One ml of a test suspension containing about $10^8$ cfu of the test microorganism per ml is added to 8 ml of the composition to be tested, and 1 ml milli-Q water is added. After 1, 2, 3 and/or and 5 minutes contact time, the amount of viable bacteria was determined by putting 0.1 ml onto a plate with a growth medium, after which the plate incubated for at least 24 hours.

Similarly, the fungicidal activity was tested in a EN 1650 suspension test, the mycobactericidal activity was tested in a EN 14348 suspension test and the virucidal activity was tested in a EN 14476 suspension test, tailored to the specific viruses.

In some experiments, a protein load was added to the suspension according to the EN 1276, EN 1650 or EN 14348 procedure to simulate unclean practical conditions. To provide for a clean condition 0.3% Bovine Albumin was added and for a dirty condition 3% Bovine Albumin.

Explanation of the compounds used:
AKYPO LF 2 C8; n=8, ex KAO Corporation
AKYPO LF 4 C6-8; n=4-9 (avg. 7), ex KAO Corporation
Monafax 1214 C8-C10, 5 EO alkyl etherphosphate ester, ex Uniqema
Barlox 10s N,N-dimethyldecylamine N-oxide, ex Lonza Inc.
Mackam LHS Lauryl hydroxysultaine, ex McIntyre
Dequest 2010 Hydroxyethylidene 1,1-diphosphonic acid, ex Solutia
Zetesol NL-U Sodium Lauryl Ether Sulphate, ex Zschimmer & Schwarz
Mackam CB 818 Cocamidopropyl Betaine, ex McIntyre Example 1

Various compositions were tested for biocidal activity and compared to standard, commercially available $H_2O_2$ solutions without any additions except for the stabilizers added by the manufacturer. The compositions of the invention tested included the compound of Formula 1 in various forms as sourced from KAO Chemicals (trade names AKYPO LF2 and AKYPO LF4). The pH of such solution ranges between 2.5 and 3.5. The test results are presented in Table 1 below. It appears that the addition of compounds according Formula 1 significantly enhances the biocidal activity of the composition.

TABLE 1

| Strain Name | Type | CFU's Suspension | 1 Min. | 3 Min. | 5 Min. |
|---|---|---|---|---|---|
| 1.30% Hydrogen Peroxide 0.5% AKYPO LF 2 | | | | | |
| Salmonella typhimurium | ATCC 27853 | 8,20E + 08 | 0 | 0 | 0 |
| Escherichia coli | ATCC 25922 | 7,50E + 07 | 0 | 0 | 0 |
| Pseudornonas aeruginosa | ATCC 27853 | 3,34E + 09 | 0 | 0 | 0 |
| Staphylococcus aureus | ATCC 25923 | 1,43E + 10 | 0 | 0 | 0 |
| Enterobacter cloacae | ATCC 13047 | 1,27E + 10 | 2 | 0 | 0 |
| Lysteria monocytogenes | ATCC 7644 | 4,22E + 09 | 0 | 0 | 0 |
| Micrococcus luteus | ATCC 9341 | 3,93E + 09 | 0 | 0 | 0 |
| Proteus vulgaris | ATCC 6380 | 2,08E + 09 | 0 | 0 | 0 |
| 1.50% Hydrogen Peroxide 0.2% AKYPO LF 2 | | | | | |
| Salmonella typhimurium | ATCC 27853 | 8,20E + 0B | 0 | 0 | 0 |
| Escherichia coli | ATCC 25922 | 7,50E + 07 | 0 | 0 | 0 |
| Pseudomonas aeruginosa | ATCC 27853 | 3,34E + 09 | 0 | 0 | 0 |
| Staphylococcus aureus | ATCC 25923 | 1,43E + 10 | 0 | 0 | 0 |
| Enterobacter cloacae | ATCC 13047 | 1,27E + 10 | 5 | 0 | 0 |
| Lysteria monocytogenes | ATCC 7644 | 4,22E + 09 | 0 | 0 | 0 |
| Micrococcus luteus | ATCC 9341 | 3,93E + 09 | 0 | 0 | 0 |
| Proteus vulgaris | ATCC 6380 | 2,08E + 09 | 0 | 0 | 0 |
| 0.50% Hydrogen Peroxide 0.20% AKYPO LF 2 | | | | | |
| Salmonella typhimurium | ATCC 27853 | 1,45E + 09 | 3 | 0 | 0 |
| Escherichia coli | ATCC 25922 | 1,40E + 07 | 0 | 0 | 0 |
| Pseudomonas aeruginosa | ATCC 27853 | 1,05E + 08 | 0 | 0 | 0 |
| Staphylococcus aureus | ATCC 25923 | 7,00E + 09 | 0 | 0 | 0 |
| Enterobacter cloacae | ATCC 13047 | 1,37E + 10 | 0 | 0 | 0 |
| 1.00% Hydrogen Peroxide 0.50% AXYPO LF 4 | | | | | |
| Salmonella typhimurium | ATCC 27853 | 3,20E + 08 | 0 | 0 | 0 |
| Escherichia coli | ATCC 25922 | 1,50E + 07 | 0 | 0 | 0 |
| Pseudomonas aeruginosa | ATCC 27853 | 2,30E + 08 | 0 | 0 | 0 |
| Staphylococcus aureus | ATCC 25923 | 7,50E + 07 | 0 | 0 | 0 |
| Enterobacter cloacae | ATCC 13047 | 2,15E + 08 | 0 | 0 | 0 |
| Lysteria monocytogenes | ATCC 7644 | 3,40E + 08 | 0 | 0 | 0 |
| 1.50% Hydrogen Peroxide 0.10% AKYPO LF 4 | | | | | |
| Salmonella typhimurium | ATCC 27853 | 3,20E + 08 | 0 | 0 | 0 |
| Escherichia coli | ATCC 25922 | 1,50E + 07 | 7 | 0 | 0 |
| Pseudomonas aeruginosa | ATCC 27853 | 2,30E + 08 | 0 | 0 | 0 |
| Staphylococcus aureus | ATCC 25923 | 7,50E + 07 | 10 | 0 | 0 |
| Enterobacter cloacae | ATCC 13047 | 2,15E + 08 | 0 | 0 | 0 |
| Lysteria monocytogenes | ATCC 7644 | 3,40E + 08 | 23 | 0 | 0 |
| 0.50% Hydrogen Peroxide 0.10% AKYPO LF 4 | | | | | |
| Salmonella typhimurium | ATCC 27853 | 1,45E + 09 | 664 | 126 | 4 |
| Escherichia coli | ATCC 25922 | 1,40E + 07 | 0 | 0 | 0 |
| Pseudomonas aeruginosa | ATCC 27853 | 1,05E + 08 | 0 | 0 | 0 |
| Staphylococcus aureus | ATCC 25923 | 7,00E + 09 | 0 | 0 | 0 |
| Enterobacter cloacae | ATCC 13047 | 1,37E + 10 | 178 | 0 | 0 |
| 0.50% Hydrogen Peroxide 0.20% AKYPO LF 4 | | | | | |
| Salmonella typhimurium | ATCC 27853 | 1,45E + 09 | 4 | 0 | 0 |
| Escherichia coli | ATCC 25922 | 1,40E + 07 | 0 | 0 | 0 |
| Pseudomonas aeruginosa | ATCC 27853 | 1,05E + 08 | 0 | 0 | 0 |
| Staphylococcus aureus | ATCC 25923 | 7,00E + 09 | 0 | 0 | 0 |
| Enterobacter cloacae | ATCC 13047 | 1,37E + 10 | 0 | 0 | 0 |

As a comparison with pure hydrogen peroxide, the following concentrations of hydrogen peroxide (Table 2) were tested for their antimicrobial efficacy. The solutions were buffered with phosphoric acid to pH 3. As can be seen from Tables 1 and 2, the addition of the compound of Formula 1 significantly enhances the biocidal activity of the composition.

TABLE 2

| Strain Name | Suspension | CFU's | | |
|---|---|---|---|---|
| | | 1 Min. | 3 Min. | 5 Min. |
| Salmonella typhimurium | 4.00E+07 0.5% $H_2O_2$ | >1000 | >1000 | 448 |
| | 3.20E+08 1% $H_2O_2$ | >1000 | >1000 | 1008 |
| | 4.80E+08 1.5% $H_2O_2$ | >1000 | >1000 | 1000 |
| | 4.80E+08 1.75% $H_2O_2$ | >1000 | >1000 | >1000 |
| | 4.80E+08 2% $H_2O_2$ | >1000 | >1000 | 1000 |
| Escherichia coli | 5.50E+07 0.5% $H_2O_2$ | >1000 | 1000 | 420 |
| | 1.50E+07 1% $H_2O_2$ | 1000 | 1000 | 768 |
| | 6.00E+07 1.5% $H_2O_2$ | 1000 | 430 | 688 |
| | 6.00E+07 1.75% | 688 | 102 | 54 |
| | 5.50E+07 2% $H_2O_2$ | 69 | 54 | 4 |
| Pseudomonas aeruginosa | 1.25E+08 0.5% $H_2O_2$ | >1000 | 221 | 3 |
| | 1.25E+08 1% $H_2O_2$ | >1000 | 431 | 72 |
| | 1.25E+08 1.5% $H_2O_2$ | 130 | 13 | 0 |
| | 1.25E+08 1.75% $H_2O_2$ | 27 | 4 | 2 |
| | 1.25E+08 2% $H_2O_2$ | 35 | 23 | 0 |
| Staphylococcus aureus | 1.50E+08 0.5% $H_2O_2$ | >1000 | >1000 | >1000 |
| | 7.50E+07 1% $H_2O_2$ | >1000 | 1072 | 608 |
| | 5.35E+08 1.5% $H_2O_2$ | >1000 | >1000 | 419 |
| | 5.35E+08 1.75% $H_2O_2$ | 672 | 344 | 22 |
| | 5.35E+08 2% $H_2O_2$ | 592 | 328 | 92 |
| Enterobacter cloacea | 2.15E+08 0.5% $H_2O_2$ | >1000 | >1000 | 892 |
| | 7.50E+08 1% $H_2O_2$ | >1000 | >1000 | 1000 |
| | 7.50E+08 1.5% $H_2O_2$ | >1000 | >1000 | 664 |
| | 7.50E+08 1.75% $H_2O_2$ | >1000 | >1000 | 320 |
| | 2.15E+08 2% $H_2O_2$ | >1000 | 200 | 120 |

It was surprisingly found that a composition of the current invention not only showed good bactericidal activity, but also good fungicidal, mycobacteridal activity and virucidal activity, whereas other known antimicrobial combinations of hydrogen peroxide and specific phosphoric acid surfactants did not exhibit any relevant reduction, especially against fungi and mycobacteria.

Example 2

A composition consisting of 5% hydrogen peroxide and 2.5% Akypo LF 2 was tested against *Mycobacterium terrae* ATCC 15755 and showed a log reduction in both clean and dirty conditions according EN 14348 of >5 in 15 minutes contact time. A combination of 5% hydrogen peroxide and 3% of a surfactant with known antimicrobial activity, namely Monafax 1214 from Uniqema (a C8-C10, 5 EO alkyl ether phosphate ester) only showed a reduction of log 1.5 after 15 minutes and log 2-3 after 30 minutes. Thus, the composition advantageously can be used as a high level disinfectant (HLD) in for instance healthcare applications.

Example 3

In order to enhance the cleaning efficacy, the composition may be supplemented with a non-ionic or amphoteric surfactant. A composition with enhanced degreasing and cleaning efficacy consisting of 2% hydrogen peroxide, 0.9% Akypo LF 4 and 0.6% Amine Oxide (Barlox 10s of Lonza Inc.) was tested against various microbial strains and showed the following log reductions in a EN 1276 suspension test, after 3 minutes contact time:

| *Escherichia coli* | ATCC 10536 | >6.7 |
| *Pseudomonas aeruginosa* | ATCC 15442 | >6.3 |
| *Staphylococcus aureus* | ATCC 6538 | >6.6 |
| *Enterococcus hirae* | ATCC 10541 | >6.5 |

Example 4

A composition consisting of 1.8% hydrogen peroxide, 0.6% Akypo LF 2 and 0.8% hydroxysultaine (Mackam LHS of McIntyre) was tested against *Candida Albicans* ATCC 12031 and showed a log 4 reduction after 15 minutes and a >log 5.3 after 30 minutes.

Example 5

A composition consisting of 4.5% hydrogen peroxide and 2% Akypo LF 4 was tested in a EN 1650 European suspension test and showed a >log 5 reduction after 5 minutes with *Candida albicans* ATCC 12031 and a >log 5 reduction after 15 minutes on *Aspergillus niger* ATCC 16404. A solution of 4.5% hydrogen peroxide was tested in similar conditions (EN 1650) and did not show any substantial log reduction on both *Candida albicans* and *Aspergillus niger* after 15 minutes. Thus, the composition can be used as a broad-spectrum disinfectant.

Example 6

In order to evaluate the virucidal activity of the compositions, a composition consisting of a low concentrated of 1% hydrogen peroxide and 0.4% Akypo LF2 was tested against the following enveloped viruses: Vaccinia virus and the Bovine Virus Diarrhea Virus (BVDV) and showed in a EN 14476 suspension test a greater than log 4 reduction after only 1 minute.

Example 7

In order to compare the bactericidal activity of compositions comprising hydrogen peroxide and either an ether carboxylic acid, a carboxylic acid, an anionic surfactant, or an amphoteric surfactant, compositions I-X were prepared (Table 3) and tested for bactericidal activity. It is clearly shown (Table 4) that a composition comprising hydrogen peroxide in combination with an ether carboxylic acid displays the highest antibacterial activity.

TABLE 3

| No. | Composition | pH |
|---|---|---|
| I | 1.5% $H_2O_2$ + 0.3% Akypo LF 4 | 2.8 |
| II | 1.5% $H_2O_2$ + 0.3% 2-Furoic Acid | 2.4 |
| III | 1.5% $H_2O_2$ + 0.3% Glycolic Acid | 2.6 |
| IV | 1.5% $H_2O_2$ + 0.3% Dequest 2010 | 2.3 |
| V | 1.5% $H_2O_2$ + 0.3% Citric Acid | 2.3 |
| VI | 1.5% $H_2O_2$ + 0.4% Lactic Acid | 2.5 |
| VII | 1.5% $H_2O_2$ + 0.4% Akypo LF 4 | 2.9 |
| VIII | 1.5% $H_2O_2$ + 0.4% Zetesol NL-U (+$H_3PO_4$ to pH 3) | 2.9 |
| IX | 1.5% $H_2O_2$ + 0.4% Mackam CB 818 (+$H_3PO_4$ to PH 3) | 3.0 |
| X | 2% $H_2O_2$ (+HCl to pH 2.5) | 2.5 |

TABLE 4

| | EN 1276 Dirty Conditions | | | | | |
| --- | --- | --- | --- | --- | --- | --- |
| | E. coli | | Staph. aureus | | Ent. cloacae | |
| Start | $1.6 \times 10^8$ | | $3.3 \times 10^7$ | | $2.4 \times 10^7$ | |
| | 1 min | 3 min | 1 min | 3 min | 1 min | 3 min |
| I | 164 | 0 | 432 | 165 | 58 | 0 |
| II | >1000 | 101 | >1000 | >1000 | >1000 | 104 |
| III | >1000 | 260 | >1000 | >1000 | >1000 | >1000 |
| IV | >1000 | 150 | >1000 | >1000 | >1000 | >1000 |
| V | >1000 | 280 | >1000 | >1000 | >1000 | >1000 |
| VI | >1000 | 290 | >1000 | >1000 | >1000 | >1000 |
| VII | 18 | 0 | 6 | 0 | 0 | 0 |
| VIII | 68 | 9 | >1000 | >1000 | 42 | 6 |
| IX | >1000 | >1000 | >1000 | 280 | >1000 | >1000 |
| X | >1000 | >1000 | >1000 | >1000 | >1000 | >1000 |

The invention claimed is:

1. A composition comprising hydrogen peroxide in a concentration of 0.05-50% (w/w) and a compound with a structure according to Formula 1:

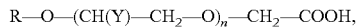

R—O—(CH(Y)—CH$_2$—O)$_n$—CH$_2$—COOH, wherein R is an alkyl or alkenylene radical containing 6-10 carbon atoms, Y is H or CH$_3$, and n is 3-10, in a concentration of 0.01-60% (w/w), with the provision that the composition does not contain acetic acid at a concentration of 0.001% or higher and/or peracetic acid at a concentration of 0.0005% or higher.

2. The composition of claim 1, wherein R is a straight chain alkyl radical.

3. The composition of claim 1 wherein n is 3-8.

4. The composition of claim 1 wherein Y is H.

5. The composition of claim 1, wherein the hydrogen peroxide concentration is 0.05-8% (w/w).

6. The composition of claim 1, wherein the concentration of the compound with a structure according to Formula 1 is 0.01-10% (w/w).

7. The composition of claim 1, wherein the concentration of hydrogen peroxide and the compound with a structure according to Formula 1 is chosen in such a way that the weight ratio between hydrogen peroxide and the compound with a structure according to Formula 1 varies between 10 and 0.1.

8. The composition of claim 1, wherein the pH has a value of 1-7.

9. The composition of claim 1 further comprising a hydrogen peroxide stabilizer, preferably in a concentration from 0.01 to 20% (w/w).

10. The composition of claim 1 further comprising a carboxylic acid, preferably in a concentration from 0.01 to 10% (w/w).

11. The composition of claim 1 further comprising a nonionic, cationic, amphoteric and/or an anionic surfactant, preferably in a concentration from 0.005 to 40% (w/w).

12. The composition of claim 11 wherein the surfactant is chosen from the group of alkyl betaines, alkyl amidopropyl betaine amides, alkyl amidopropyl betaines and amine oxides.

13. The composition of claim 1 further comprising a corrosion inhibitor, preferably in a concentration from 0.01 to 20% (w/w).

14. A method for any purpose where disinfecting and/or sanitizing and/or preservative activity is required, optionally in combination with cleaning and/or bleaching activity, comprising using the composition of claim 1.

15. A method for disinfecting and/or sanitizing and/or preserving a substrate comprising contacting the substrate with an effective amount of the biocidal composition of claim 1.

16. The method of claim 15, wherein the contacting comprises spraying, dipping, fogging and/or rinsing.

17. The composition of claim 1, wherein the hydrogen peroxide concentration is 0.1-5%.

18. The composition of claim 1, wherein the hydrogen peroxide concentration is 0.3-2%.

19. The composition of claim 1, wherein the concentration of the compound with a structure according to Formula 1 is 0.02-5%.

20. The composition of claim 1, wherein the concentration of the compound with a structure according to Formula 1 is 0.05-2%.

21. The composition of claim 1, wherein the concentration of hydrogen peroxide and the compound with a structure according to Formula 1 is chosen in such a way that the weight ratio between hydrogen peroxide and the compound with a structure according to Formula 1 varies between 5 and 0.2.

22. The composition of claim 1, wherein the concentration of hydrogen peroxide and the compound with a structure according to Formula 1 is chosen in such a way that the weight ratio between hydrogen peroxide and the compound with a structure according to Formula 1 varies between 2 and 0.5.

23. The composition of claim 1, wherein the pH has a value of 1.5-6.

24. The composition of claim 1, wherein the pH has a value of 1.5-5.

25. The composition of claim 9, wherein the hydrogen peroxide stabilizer is a cation sequestering agent.

* * * * *